United States Patent
Hottovy et al.

(10) Patent No.: US 8,617,123 B2
(45) Date of Patent: Dec. 31, 2013

(54) PRE-FILLED ACTIVE VIAL HAVING INTEGRAL PLUNGER ASSEMBLY

(75) Inventors: Tracy Ray Hottovy, Wilson, NC (US); Eric Schiller, Westfield, NJ (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 464 days.

(21) Appl. No.: 12/859,808

(22) Filed: Aug. 20, 2010

(65) Prior Publication Data
US 2011/0066116 A1 Mar. 17, 2011

Related U.S. Application Data

(60) Provisional application No. 61/235,836, filed on Aug. 21, 2009.

(51) Int. Cl.
*A61M 5/00* (2006.01)

(52) U.S. Cl.
USPC ............ 604/208; 222/23; 222/263; 222/389; 222/401; 222/477

(58) Field of Classification Search
USPC ................ 60/387, 409; 222/23, 41, 61, 256, 222/260–263, 389, 477, 401; 138/43; 251/208
See application file for complete search history.

(56) References Cited

U.S. PATENT DOCUMENTS

| | | | |
|---|---|---|---|
| 927,298 A * | 7/1909 | Twitchell | 73/744 |
| 1,961,490 A | 6/1934 | Hein | |
| 2,630,804 A | 3/1953 | Mende | |
| 3,604,417 A | 9/1971 | Stolzenberg et al. | |
| 3,780,693 A * | 12/1973 | Parr | 116/270 |
| 4,093,108 A | 6/1978 | Hein et al. | |
| 4,113,144 A | 9/1978 | Hein et al. | |
| 4,221,218 A | 9/1980 | Pfleger | |
| 4,323,066 A | 4/1982 | Bourdon | |
| 4,505,701 A | 3/1985 | Navato | |
| 4,583,978 A | 4/1986 | Porat et al. | |
| 4,684,366 A | 8/1987 | Denny et al. | |
| 4,773,900 A | 9/1988 | Cochran | |
| 4,915,693 A | 4/1990 | Hessel | |
| 5,009,637 A | 4/1991 | Newman et al. | |
| 5,017,190 A * | 5/1991 | Simon et al. | 604/207 |
| 5,041,094 A | 8/1991 | Perego et al. | |
| 5,053,019 A | 10/1991 | Duffy | |
| 5,140,982 A * | 8/1992 | Bauman | 128/205.13 |
| 5,312,389 A | 5/1994 | Theeuwes et al. | |
| 5,779,678 A | 7/1998 | Carter | |

(Continued)

FOREIGN PATENT DOCUMENTS

| EP | 0 600 754 A2 | 6/1994 |
|---|---|---|
| EP | 1 208 858 A1 | 5/2002 |
| EP | 1 535 639 A1 | 6/2005 |

*Primary Examiner* — Kevin P Shaver
*Assistant Examiner* — Patrick M Buechner
(74) *Attorney, Agent, or Firm* — The Webb Law Firm

(57) ABSTRACT

A pre-filled vial assembly adapted for dispensing and delivering a fluid includes: a body member having a distal end, a proximal end, and a sidewall extending therebetween defining an interior; and a transitionable stopper disposed within the interior of the body member. At least a portion of the body member is engageable with a source of air or fluid for advancing the transitionable stopper from an initial position to an activated position in which at least a portion of a fluid contained within the interior of the body member is advanced therefrom.

10 Claims, 11 Drawing Sheets

(56) References Cited

U.S. PATENT DOCUMENTS

| | | |
|---|---|---|
| 5,868,713 A | 2/1999 | Klippenstein |
| 5,879,336 A | 3/1999 | Brinon |
| 5,954,695 A | 9/1999 | Sims et al. |
| 6,123,685 A | 9/2000 | Reynolds |
| 6,139,530 A | 10/2000 | Hiejima et al. |
| 6,331,173 B1 | 12/2001 | Ljungquist |
| 6,685,673 B2 | 2/2004 | Minezaki et al. |
| 6,890,320 B2 | 5/2005 | Minezaki |
| 7,374,556 B2 | 5/2008 | Mallett |
| 2002/0165490 A1 | 11/2002 | Minezaki et al. |
| 2003/0216695 A1 | 11/2003 | Yang |
| 2003/0233070 A1* | 12/2003 | De La Serna et al. ........ 604/141 |
| 2004/0019325 A1 | 1/2004 | Shekalim |
| 2005/0070848 A1 | 3/2005 | Kim et al. |
| 2009/0177158 A1 | 7/2009 | Krumme et al. |

* cited by examiner

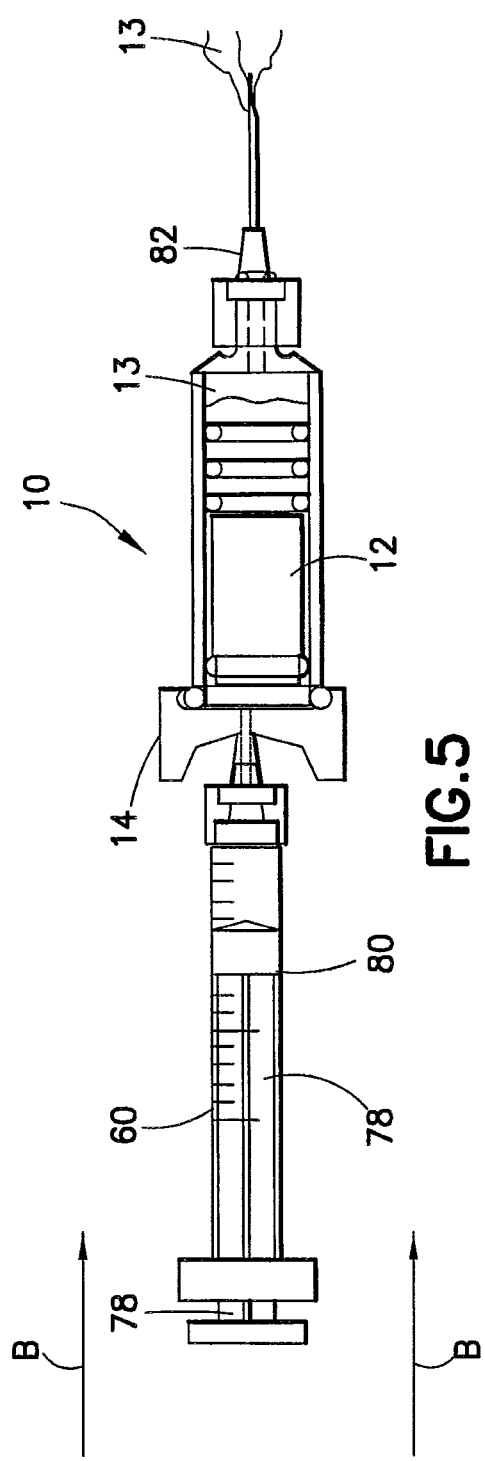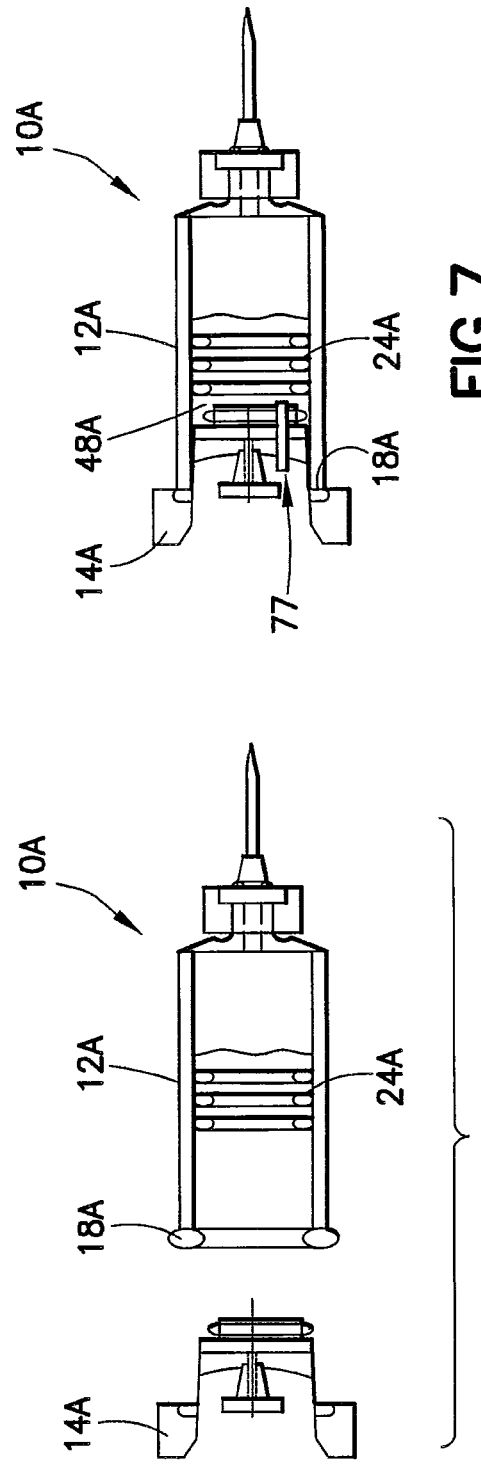
FIG. 5
FIG. 6
FIG. 7

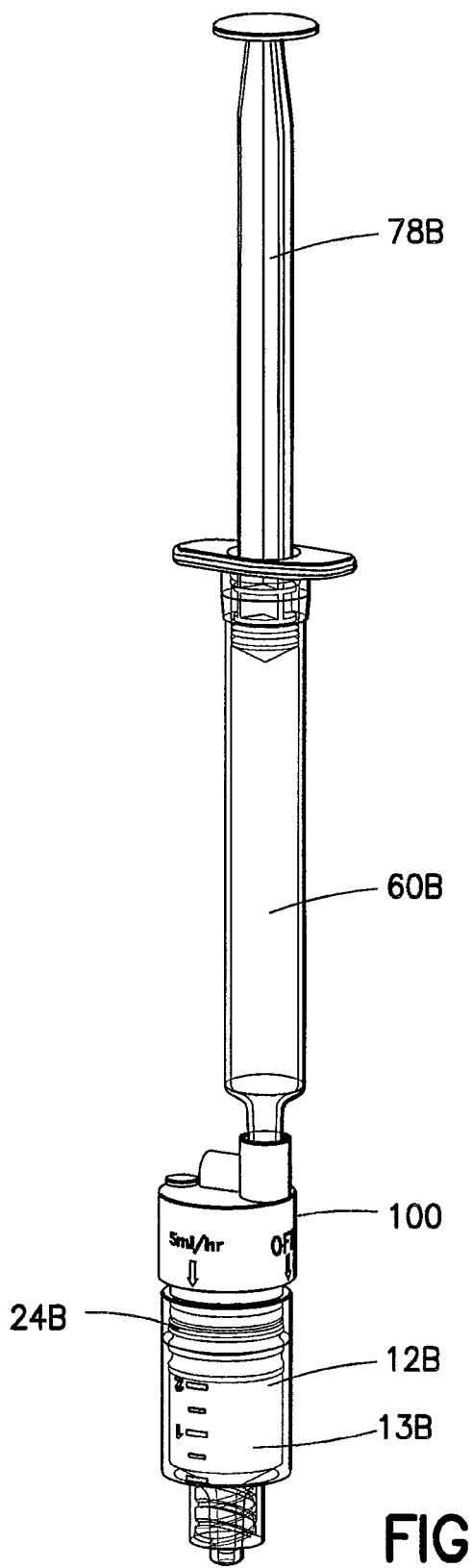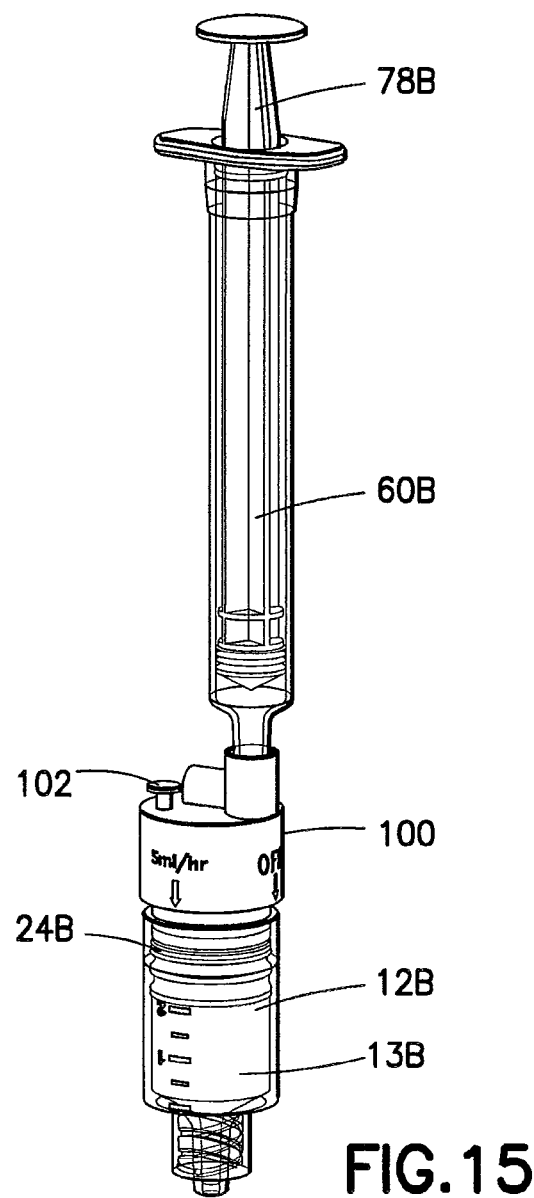

PRE-FILLED ACTIVE VIAL HAVING INTEGRAL PLUNGER ASSEMBLY

CROSS REFERENCE TO RELATED APPLICATIONS

This application claims priority to U.S. Provisional Patent Application Ser. No. 61/235,836 entitled "Pre-Filled Active Vial Having Integral Plunger Assembly" filed Aug. 21, 2009, the entire disclosure of which is hereby incorporated by reference.

BACKGROUND OF THE INVENTION

1. Field of the Invention

The present invention is directed to a pre-filled vial assembly adapted for dispensing and delivery of a fluid. More particularly, the present invention is directed to a pre-filled active vial having an integral plunger assembly for delivering a fluid that may be directly attached to a standard hypodermic syringe. A regulator for regulating the release of air from the pre-filled vial assembly is also disclosed.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing this syringe.

For some applications, small vials and ampoules are used to store medications and other narcotics or controlled substances. These vials and ampoules are typically storage vessels and do not typically include a plunger rod or stopper. During use, a medical practitioner draws the medication or controlled substance from the vial or ampoule by inserting the needle of a standard syringe therein and withdrawing the contents. The process of transferring the contents of a vial or ampoule into a syringe for injection increases the likelihood of contamination. In addition, as the majority of ampoules are glass, the transfer process increases the likelihood that shards of glass may become incorporated into the injected fluid.

SUMMARY OF THE INVENTION

In accordance with an embodiment of the present invention, a pre-filled vial assembly adapted for dispensing and delivering a fluid includes: a body member having a distal end, a proximal end, and a sidewall extending therebetween defining an interior; and a transitionable stopper disposed within the interior of the body member. At least a portion of the body member is engageable with a source of air or fluid for advancing the transitionable stopper from an initial position to an activated position in which at least a portion of a fluid contained within the interior of the body member is advanced therefrom.

The proximal end of the body member may include a receiving cavity. The pre-filled vial assembly may further include a luer connection having a forward end configured for engagement with the receiving cavity of the proximal end of the body member. The forward end of the luer connection may include a seal for internal sealing against a portion of the receiving cavity. At least a portion of the proximal end of the body member may include a sealing member for receipt within a portion of the luer connection.

The luer connection may include a vent. The source of air or gas may be engaged with a fluid passage formed in the luer connection. The source of air or gas may be a standard syringe, such that depression of a plunger rod of the standard syringe transitions the transitionable stopper from the initial position to the activated position to expel contents from the interior of the body member of the pre-filled vial assembly.

The distal end of the body member may include a dispensing tip having a fluid passage therethrough in communication with the interior of the body member. A dispensing cannula may be configured for engagement with the dispensing tip of the body member. The body member may include markings provided on a portion thereof for providing an indication of an amount of fluid that has been expelled during use.

In accordance with another embodiment of the present invention, a pre-filled pod assembly includes: a pre-filled pod having a distal end, a proximal end, and a sidewall extending therebetween defining an interior; a transitionable stopper disposed within the interior of the pre-filled pod; and a regulator coupled to the proximal end of the pre-filled pod and provided in fluid communication with the interior of the pre-filled pod. At least a portion of the regulator is engageable with a source of air or fluid for advancing the transitionable stopper from an initial position to an activated position in which at least a portion of a fluid contained within the interior of the pre-filled pod is advanced therefrom.

The regulator may be configured to apply a predetermined amount of pressurized air to the transitionable stopper through the use of a valve device. The source of air or gas may be engaged with an access port formed in the regulator. The source of air or gas may be a standard syringe, such that depression of a plunger rod of the standard syringe pressurizes the regulator. The regulator may further include an indicator that is activated to indicate that the regulator has a predetermined amount of pressurized air that is sufficient to deliver a complete dose. The regulator may include an activation trigger configured to be aligned with an indicator for allowing a user to set the regulator to deliver a metered dose.

In accordance with yet another embodiment of the present invention, a pre-filled pod assembly includes: a pre-filled pod having a distal end, a proximal end, and a sidewall extending therebetween defining an interior; and a capsule having a fluid contained therein and disposed within the interior of the pre-filled pod. The capsule includes a first opening adjacent a first end of the capsule and aligned with the proximal end of the pre-filled pod, and a second opening adjacent a second end of the capsule and aligned with the distal end of the pre-filled pod. The pre-filled pod assembly also includes a transitionable stopper disposed within the interior of the pre-filled pod between the proximal end of the pre-filled pod and the first end of the capsule. At least a portion of the pre-filled pod is engageable with a source of air or fluid for advancing the transitionable stopper such that air disposed between the capsule and the transitionable stopper is pressurized and enters the capsule via the first opening, thereby expelling at least a portion of the fluid from within the capsule through the second opening.

At least a portion of the transitionable stopper may seal the first opening after the transitionable stopper has advanced completely. A volume of the fluid within the capsule may be greater than a volume of air disposed between the capsule and the transitionable stopper, which limits expulsion of the air from the capsule of the pre-filled pod. The capsule may be held within the interior of the pre-filled pod in a specific orientation by at least one grommet. In addition, an air bubble may be provided adjacent to the second opening of the capsule to limit expulsion of the fluid within the capsule absent advancement of the transitionable stopper.

In accordance with still another embodiment of the present invention, a pre-filled pod assembly includes: a pre-filled pod having a distal end, a proximal end, and a sidewall extending therebetween defining an interior; and a capsule having a fluid contained therein and disposed within the interior of the pre-filled pod. The capsule includes a first opening adjacent a first end of the capsule and aligned with the proximal end of the pre-filled pod, and a second opening adjacent a second end of the capsule and aligned with the distal end of the pre-filled pod. The pre-filled pod assembly also includes: a transitionable stopper disposed within the interior of the pre-filled pod between the proximal end of the pre-filled pod and the first end of the capsule, and a regulator coupled to the proximal end of the pre-filled pod and provided in fluid communication with the interior of the pre-filled pod. The regulator is engageable with a source of air or fluid for advancing the transitionable stopper such that air disposed between the capsule and the transitionable stopper is pressurized and enters the capsule via the first opening, thereby expelling at least a portion of the fluid from within the capsule through the second opening.

At least a portion of the transitionable stopper may seal the first opening after the transitionable stopper has advanced completely. A volume of the fluid within the capsule may be greater than a volume of air disposed between the capsule and the transitionable stopper, which limits expulsion of the air from the capsule of the pre-filled pod. The capsule may be held within the interior of the pre-filled pod in a specific orientation by at least one grommet.

The regulator may be configured to apply a predetermined amount of pressurized air to the transitionable stopper through the use of a valve device. The source of air or gas may be engaged with an access port formed in the regulator. The source of air or gas may be a standard syringe, such that depression of a plunger rod of the standard syringe pressurizes the regulator. The regulator may further include an indicator that is activated to indicate that the regulator has a predetermined amount of pressurized air that is sufficient to deliver a complete dose. The regulator may include an activation trigger configured to be aligned with an indicator for allowing a user to set the regulator to deliver a metered dose.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 5 is a schematic partial cross-sectional side view of the pre-filled pod assembly and female luer connector engaged with the standard syringe of FIG. 4 in an activated position having the contents of the pod assembly partially expelled therefrom in accordance with an embodiment of the present invention.

FIG. 6 is a schematic partial cross-sectional side view of a pre-filled pod having an alternative female luer connector in accordance with an embodiment of the present invention.

FIG. 7 is a schematic partial cross-sectional side view of the pre-filled pod assembly joined with the female luer connector of FIG. 6 in accordance with an embodiment of the present invention.

FIG. 14 is a perspective view of the pre-filled pod and regulator engaged with a standard syringe of FIG. 12 in the initial position in a second cycle in accordance with an embodiment of the present invention.

FIG. 15 is a perspective view of the pre-filled pod and regulator engaged with a standard syringe of FIG. 12 in the activated position in a second cycle in accordance with an embodiment of the present invention.

DETAILED DESCRIPTION

Figure 1:
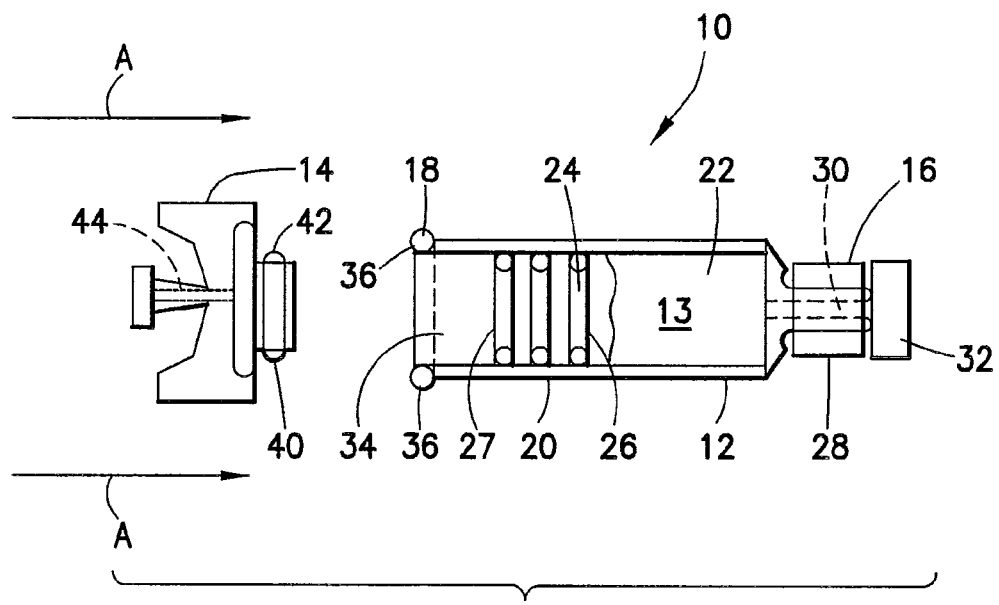
FIG. 1 is a schematic partial cross-sectional side view of a pre-filled pod assembly and a female luer connector in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1-5, which depict a pre-filled pod assembly 10 which is adapted for dispensing and delivery of a fluid. The pre-filled pod assembly 10 includes a pre-filled pod 12 and a female luer connection 14 adapted for engagement with a portion of the pre-filled pod 12. The pre-filled pod 12 has a distal end 16 and a proximal end 18 and a sidewall 20 extending therebetween defining an interior 22. The pre-filled pod 12 also includes a transitionable stopper 24 disposed at least partially within the interior 22 of the pre-filled pod 12. The transitionable stopper 24 is dimensioned for interference fit within the interior 22 of the pre-filled pod 12 to create a substantially liquid impermeable seal against the interior of the sidewall 20. In one embodiment, the transitionable stopper 24 may be a polymeric material, rubber composition, hard plastic composition, and the like.

In one embodiment, the pre-filled pod 12 is adapted for containing a substance 13 therein, such as a fluid medication, sterile water, saline, fluid narcotic, or other controlled substance. The interior 22 of the pre-filled pod 12 may have any suitable storage volume for housing a substance therein, such as 2-3 ml. It is noted that the storage volume may be exclusive of the volume occupied by the transitionable stopper 24. In one embodiment, the transitionable stopper 24 has a distal end 26 and a proximal end 27, with the suitable storage volume defined between the interior 22 of the sidewall 20 of the pre-filled pod 12 and the distal end 26 of the transitionable stopper 24. In this configuration, the transitionable stopper 24 may be made of a substantially non-reactive material so as not to interfere or interact with the substance 13 disposed within the pre-filled pod 12. Alternatively, a non-reactive coating and/or non-reactive seal member (not shown) may be disposed adjacent the distal end 26 of the transitionable stopper 24 to provide additional sealing between the transitionable stopper 24 and the contents of the pre-filled pod 12. The sidewall 20 of the pre-filled pod 12 may also be made of a substantially non-reactive material, such as glass, one or more polymeric material, and/or a polymeric material molded over glass and may optionally be coated with a barrier or other non-reactive coating.

The distal end 16 of the pre-filled pod 12 may include a dispensing tip 28 having a fluid passage 30 therethrough in communication with the interior 22 of the pre-filled pod 12. When suitable pressure is applied to the substance 13 of the interior 22 of the pre-filled pod 12, at least a portion of the substance 13 may pass through the fluid passage 30 for expulsion from the pre-filled pod 12, as will be described herein. The dispensing tip 28 may also include a removable cap 32 for sealing the fluid passage 30.

Figure 2:
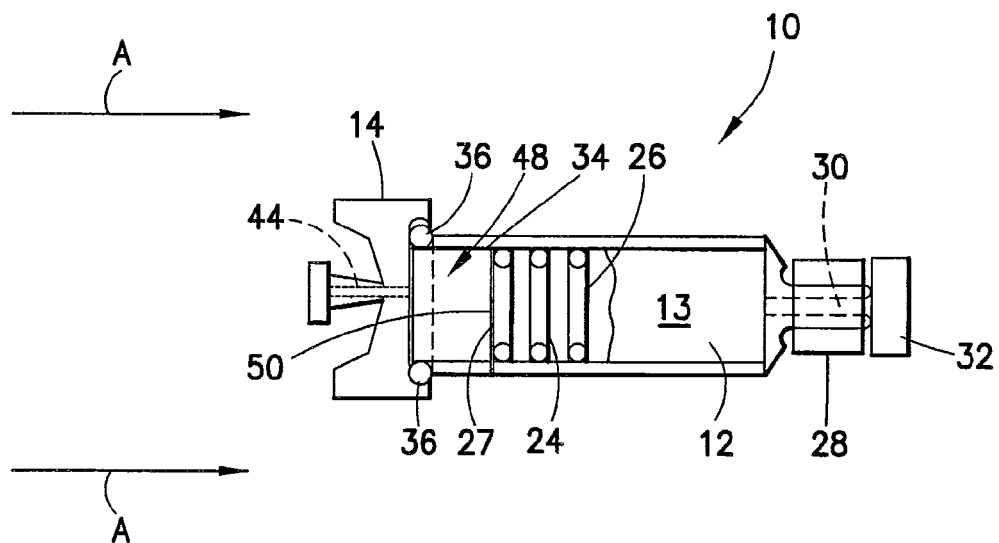
FIG. 2 is a schematic partial cross-sectional side view of the pre-filled pod assembly joined with the female luer connector of FIG. 1 in accordance with an embodiment of the present invention.

The proximal end 18 of the pre-filled pod 12 may include a receiving cavity 34 adapted for engagement with a female luer connection 14. In one configuration, at least a portion of the female luer connection 14 is adapted for receipt within the receiving cavity 34. A forward end 40 of the female luer connection 14 may include a seal 42, such as an "O-ring", for internal sealing against a portion of the receiving cavity 34. Optionally, a portion of the proximal end 18 of the pre-filled pod 12 may also include a sealing member 36 for receipt within a portion of the female luer connection 14, as shown in FIG. 2. The female luer connection 14 includes a fluid passage 44 therethrough, such that fluid, either in the form of a gas or liquid, may pass through the fluid passage 44 and contact the proximal end 27 of the transitionable stopper 24.

Engagement of the female luer connection 14 and the pre-filled pod 12 may be accomplished by applying a force in the direction of the arrows A shown in FIGS. 1-2. It is noted that in certain configurations, the engagement of the female luer connection 14 with the pre-filled pod 12 occurs after aseptic fill and terminal sterilization of the pre-filled pod 12 and indwelling substance 13. As shown in FIG. 2, a captive air chamber 48 may be formed between the female luer connection 14 and the proximal end 27 of the transitionable stopper 24. This captive air chamber 48 may be open to the atmosphere. Optionally, a disk member 50, such as a metalized disk, may be provided adjacent the proximal end 27 of the transitionable stopper 24 to assist in barrier and/or structural integrity of the transitionable stopper 24.

Figure 3:
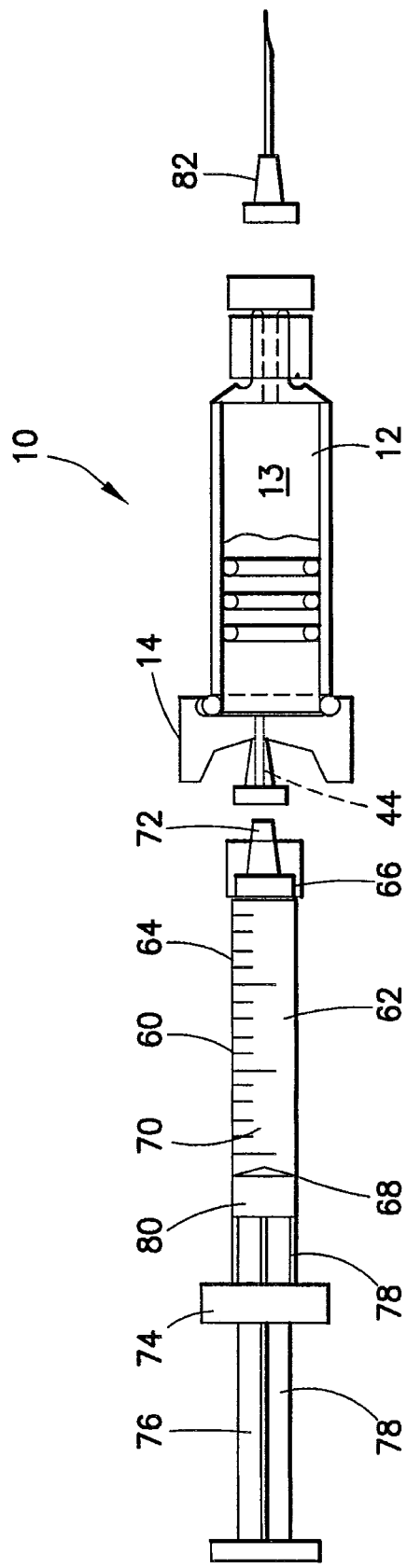
FIG. 3 is a schematic partial cross-sectional side view of the pre-filled pod assembly and female luer connector of FIG. 2 engageable with a standard syringe in accordance with an embodiment of the present invention.
Figure 4:
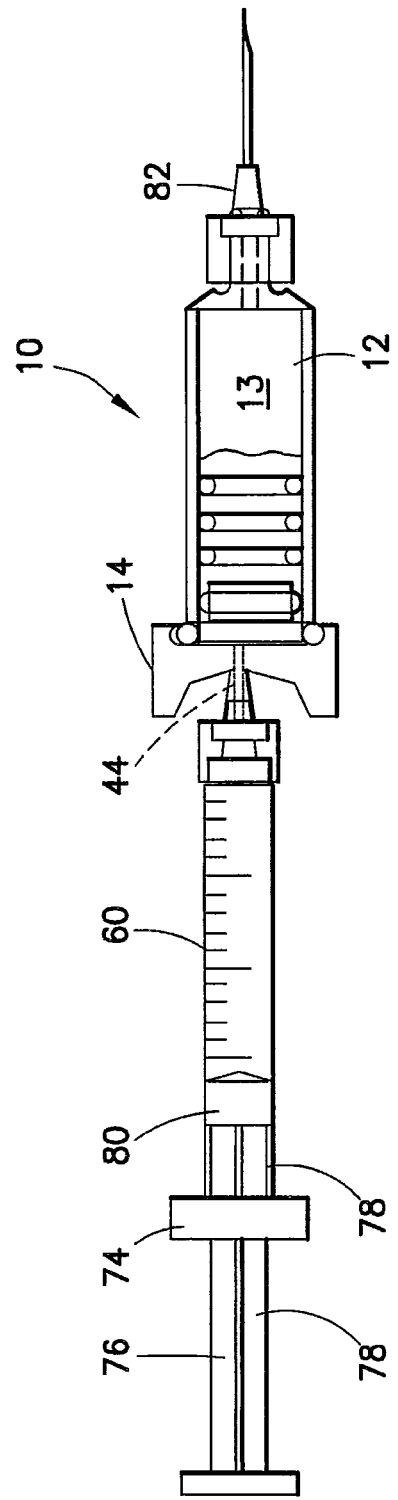
FIG. 4 is a schematic partial cross-sectional side view of the pre-filled pod assembly and female luer connector of FIG. 2 engaged with the standard syringe of FIG. 3 in an initial position in accordance with an embodiment of the present invention.

As shown in FIGS. 3-5, a source of air or gas, such as a standard syringe assembly 60, may be engaged with the female luer connection 14. The standard syringe assembly 60 may include a syringe barrel 62 defined by barrel wall 64 extending between a forward or distal end 66 and a rearward or proximal end 68, thereby defining interior chamber 70 of syringe barrel 62. Syringe barrel 62 may be in the general form of an elongated cylindrical barrel as is known in the art for the general shape of a hypodermic syringe. Forward end 66 of syringe barrel 62 includes an outlet opening 72 which is provided in fluid communication with the fluid passage 44 of the luer connection 14, such that once engaged, the interior chamber 70 of the syringe barrel 62 is provided in fluid communication with the fluid passage 44 of the luer connection 14. As used herein, the term "fluid" is intended to include both gases and liquids.

The syringe barrel 62 may include markings, such as graduations on the wall thereof, for providing an indication as to the level or amount of fluid contained within syringe barrel 62. Such markings may be provided on the external wall, the internal wall, or integrally formed or otherwise within the wall of syringe barrel 62. The syringe barrel 62 may further include a finger grasping surface, such as finger flanges 74 for providing finger support surfaces for a user during use of syringe assembly 60. The syringe assembly 60 further includes a plunger assembly 76, a portion of which is disposed at least partially within syringe barrel 62. Plunger assembly 76 provides a mechanism for dispensing fluid contained within the interior chamber 70 of syringe barrel 62. In particular, plunger assembly 76 includes a plunger rod 78 connected to a plunger head 80 adapted for expelling contents of the interior chamber 70 when the plunger rod is pushed in the direction of arrow B, as shown in FIG. 5.

A dispensing cannula 82, such as a patient needle or IV system needle, may be adapted for engagement with the distal end 16 of the pre-filled pod 12, such as the dispensing tip 28. As shown in FIG. 5, when the plunger rod 78 is deployed in the direction of arrow B, fluid, preferably air, is expelled from the interior chamber 70 of the syringe barrel 62 and directed through the fluid passage 44 of the luer connection 14. The fluid exiting the interior chamber 70 is pressurized by the action of the plunger rod 78 and contacts the proximal end 27 of the transitionable stopper 24 with sufficient pressure to advance the transitionable stopper 24 from an initial position, as shown in FIG. 4, to an activated position, shown in FIG. 5 in which the substance 13 of the pre-filled pod 12 is expelled from the pre-filled pod. It is noted that the syringe assembly 60 does not directly contact any of the substance 13 contained within the pre-filled pod 12 and thus, after use of the pre-filled pod 12, the syringe assembly 60 may be re-used. It is also noted that the interior chamber 70 of the syringe assembly 60 may utilize either a gas or a liquid, or both, to advance the transitionable stopper 24. In another configuration, a vent (not shown) may be provided in the proximal end 18 of the pre-filled pod 12 to allow injection of a liquid into the captive air chamber 48 to allow the attachment of a standard syringe assembly 60 and subsequent drug delivery pump (also not shown) for metered dosing.

An advantage of using a pre-filled pod 12 of the present invention is the small storage space of the pre-filled pod. For example, a large disadvantage of a pre-filled syringe with a vaccine is that most vaccines need to be kept in cold storage during transport and prior to use. The small size of the pre-filled pods of the present invention allows pre-filling with a pre-loaded dose of vaccine that may be easily kept in cold storage. Most institutions have limited space of cold storage and this design facilitates low storage space. Accordingly, when the pre-filled pods are used for pre-filling for "developing countries" in support of vaccination campaigns, the reduced size of the device for cold storage transport, and the lack of a plunger rod being attached to the stopper, makes the device less desirable for improper re-use of a contaminated product.

Additional advantages of the present invention are a reduction in the number of components required to complete a dispensing of a substance, and that a medical practitioner cannot draw the transitionable stopper 24 toward the proximal end of the pre-filled pod. It is also noted herein that the dispensing cannula 82 and the female luer connection 14 may be appropriately adapted for engagement with any standard system conventionally known. For example, many pharmaceutical preparations are manufactured using syringe filling equipment along with nest filling equipment where the syringes are supplied in a nest holder to the pharmaceutical manufacturer. The active vial design of the present invention with the included flange on the open end and standard stopper design facilitates the use of existing syringe filling equipment.

Figure 8:
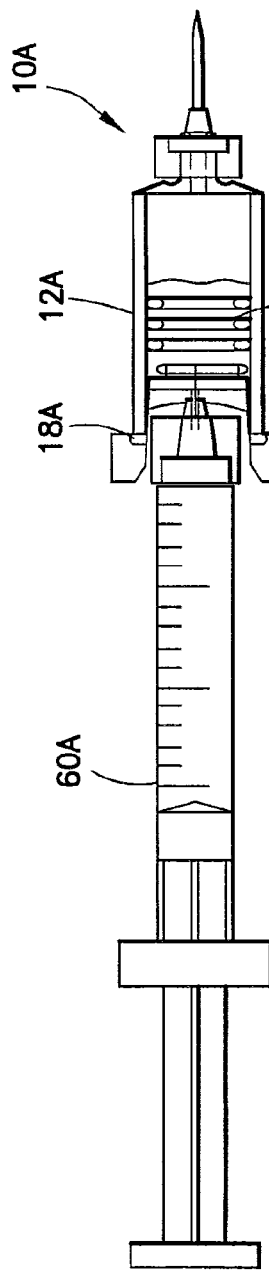
FIG. 8 is a schematic partial cross-sectional side view of the pre-filled pod assembly and female luer connector of FIG. 7 engaged with a standard syringe in accordance with an embodiment of the present invention.

Referring to FIGS. 6-8, an alternative connection between the proximal end 18A of the pre-filled pod 12A and the female luer connection 14A is shown. In this configuration, the female luer connection 14A may be dimensioned to at least partially recess into the proximal end 18A of the pre-filled pod 12A to further reduce the overall operating dimensions of the pre-filled pod assembly 10A. As shown in FIG. 8, the syringe assembly 60A may also be at least partially recessed into the proximal end 18A of the pre-filled pod 12A. In a further configuration, with reference to FIG. 7, the female luer connection 14A may also include a vent 77 adapted to allow gas to escape from the captive air chamber 48A but does not allow passage of liquid therethrough. It is contemplated herein that the use of a saline filled syringe assembly 60A could allow the pre-filled pod 12A to evacuate air and be used on a conventional hospital pump with a liquid filled behind the transitionable stopper 24A to advance the transitionable stopper 24A in a distal direction in accordance with pump movement.

It is contemplated herein that the pre-filled pod 12, 12A of the present invention is suitable for use in drug administration via an IV, dilution into an IV system, and through safety needles that can be attached for injection.

Figure 9:
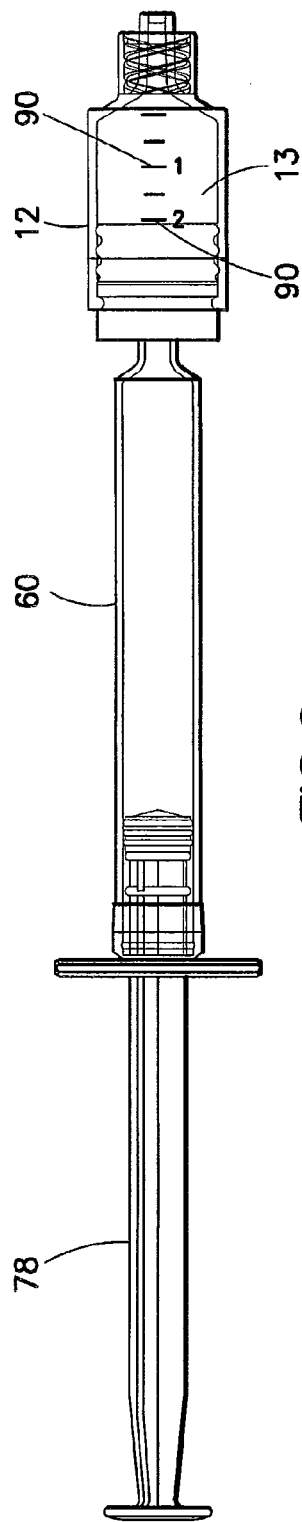
FIG. 9 is a side view of a pre-filled pod assembly and female luer connector engaged with a standard syringe in an initial position in accordance with an embodiment of the present invention.
Figure 10:
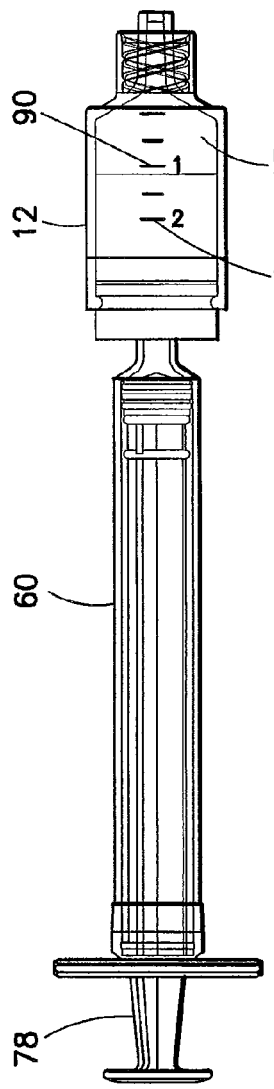
FIG. 10 is a side view of the pre-filled pod assembly and female luer connector engaged with a standard syringe of FIG. 9 in an activated position in accordance with an embodiment of the present invention.

Referring to FIGS. 9-10, the pre-filled pod 12 of the present invention may be adapted to indicate to the user that a certain amount of substance 13 has been expelled by markings 90 provided on a portion of the pre-filled pod 12. Accordingly, the medical practitioner may observe that a complete dose corresponds to a specified amount of substance. Referring to FIG. 9, the pre-filled pod 12 is shown in the initial unused position. Referring to FIG. 10, the pre-filled pod 12 is shown having a portion of the substance partially expelled from the pre-filled pod 12 upon application of force to the plunger rod 78 of the syringe assembly 60. It is appreciated herein that although the pre-filled pod 12 and the syringe assembly 60 are shown in the drawings in a substantially horizontal orientation, in use, the pre-filled pod 12 and the syringe assembly 60 will likely be employed in an angled configuration, such as about 60° with respect to vertical.

Figure 11:
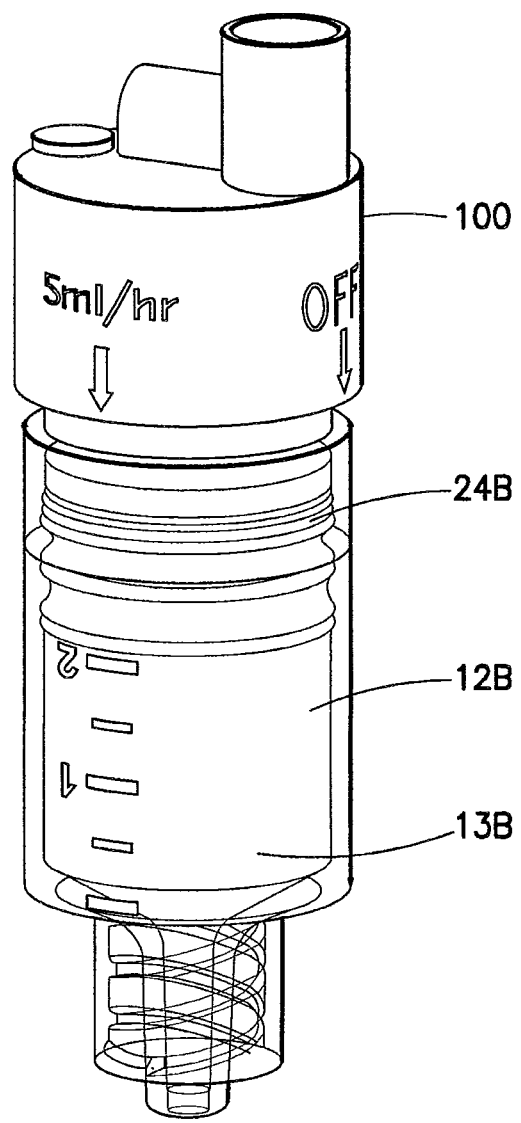
FIG. 11 is a perspective view of a pre-filled pod engaged with a regulator in accordance with an embodiment of the present invention.
Figure 12:
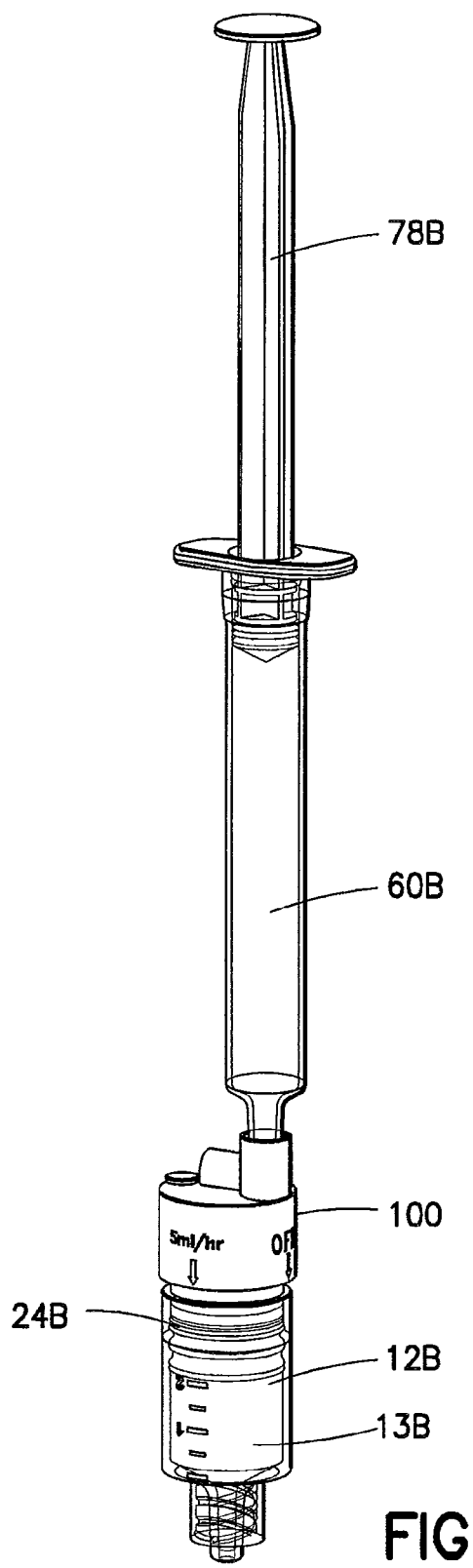
FIG. 12 is a perspective view of the pre-filled pod and regulator of FIG. 11 engaged with a standard syringe in an initial position in accordance with an embodiment of the present invention.
Figure 13:
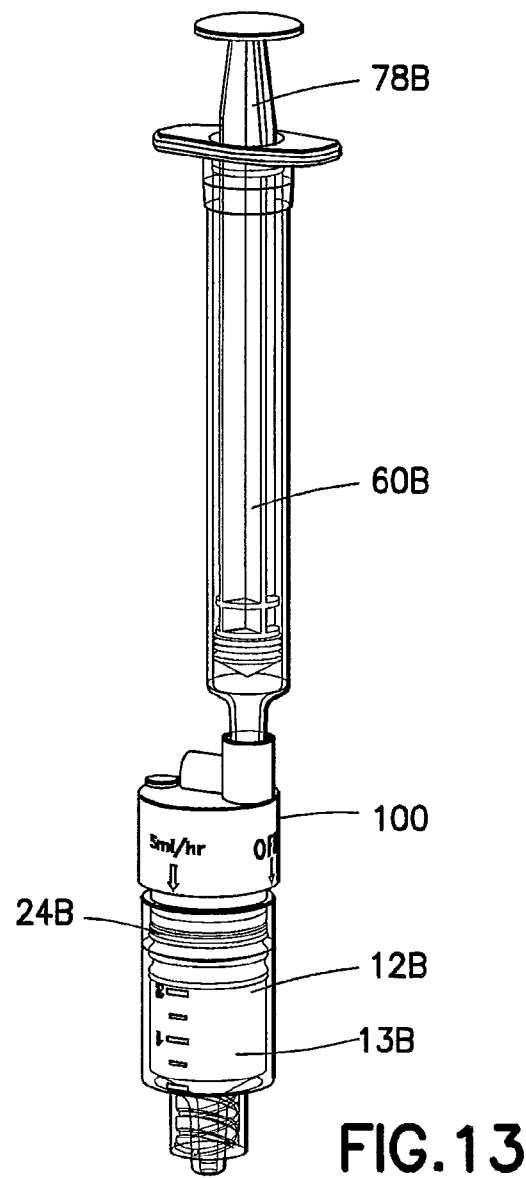
FIG. 13 is a perspective view of the pre-filled pod and regulator engaged with a standard syringe of FIG. 12 in the activated position in a first cycle in accordance with an embodiment of the present invention.

Referring to FIGS. 11-15, the pre-filled pod 12B may be used as described above in conjunction with a regulator 100 for regulating the amount of substance 13B expelled from the pre-filled pod 12B over a predetermined period of time. In certain situations, a medical practitioner may be required to introduce a substance 13B, such as a medication, narcotic, and the like, into an IV system or other similar treatment delivery system over a long period of time. Some dosing deliveries may require that a medical practitioner deliver a complete dose over a period of time on the order of five minutes by manually advancing a syringe plunger in incremental steps. This slow pacing can be difficult for a hurried medical practitioner to maintain, and consistency may be lost by human error. The regulator 100 of the present invention may be provided in fluid communication with the transitionable stopper 24B in order to provide for a constant expulsion of substance 13B from the pre-filled pod 12B over a predetermined length of time without requiring a medical practitioner to determine the pacing of the dose. As shown in FIGS. 12-14, the regulator 100 coupled with the pre-filled pod 12B of FIG. 11, is shown coupled with a standard syringe assembly 60B such that fluid, such as air, within the interior chamber 70 of the syringe assembly 60B is directed into the regulator 100, the mechanism of which will be discussed herein.

Referring to FIGS. 12-13, in use the medical practitioner determines the appropriate amount of dose that should be provided over a specified period of time. The medical practitioner may then deploy the plunger rod 78B or set an automatic plunger deployment system (not shown) to deploy the plunger rod 78B. The regulator 100 of the present invention prevents over-dosing within a specified period of time by restricting the advancement of the transitionable stopper 24B. In certain situations, a single deployment of the plunger rod 78B of the syringe assembly 60B may be sufficient to properly deliver the dose of substance 13B by pressurizing the regulator 100 in a single or first cycle. In other situations, a second cycle, shown in FIGS. 14-15, may also be required. In the second cycle, the medical practitioner re-deploys the plunger rod 78B of the syringe assembly 60B. After completion of an appropriate number of cycles, such as after completion of the second cycle, the indicator 102, shown in FIG. 15, may be activated to indicate that the regulator 100 has sufficient pressure to deliver a complete dose over a specified and predetermined period of time.

Figure 18:
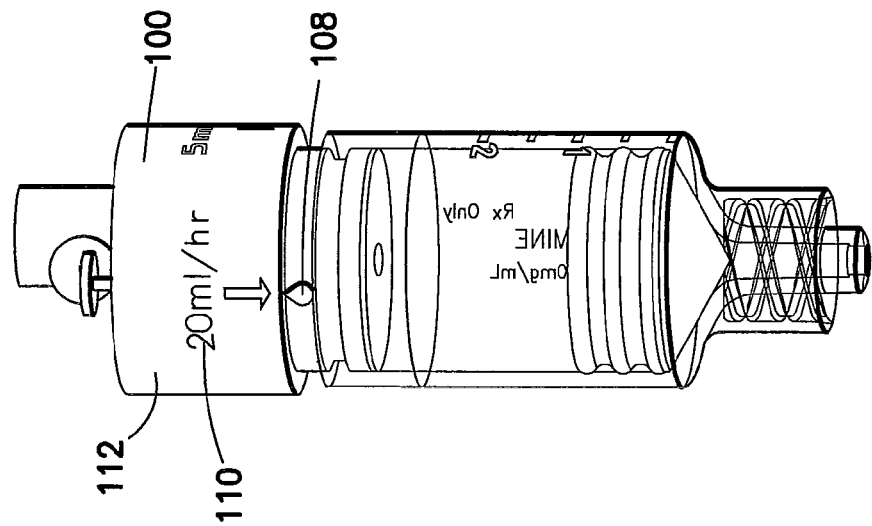
FIG. 18 is a perspective view of the pre-filled pod and regulator of FIG. 16 in an activated position having a specified speed selected in accordance with an embodiment of the present invention.
Figure 17:
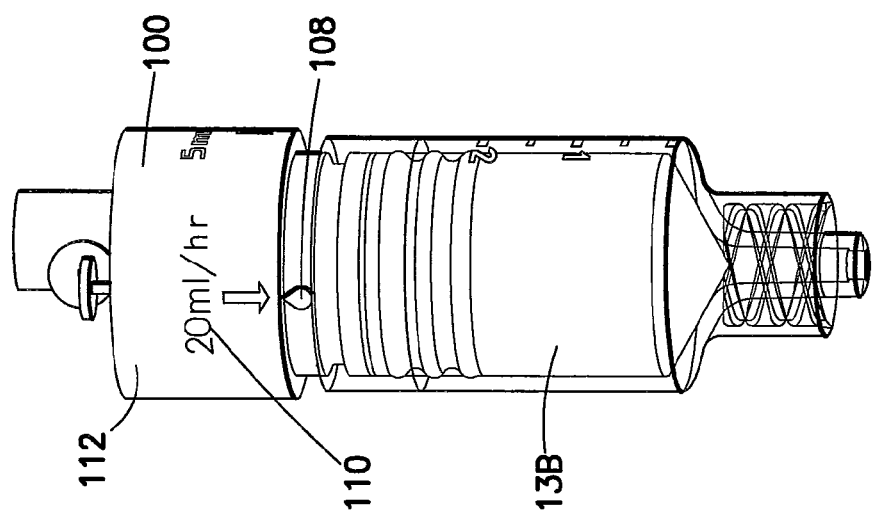
FIG. 17 is a perspective view of the pre-filled pod and regulator of FIG. 16 in an initial position having a specified speed selected in accordance with an embodiment of the present invention.
Figure 16:
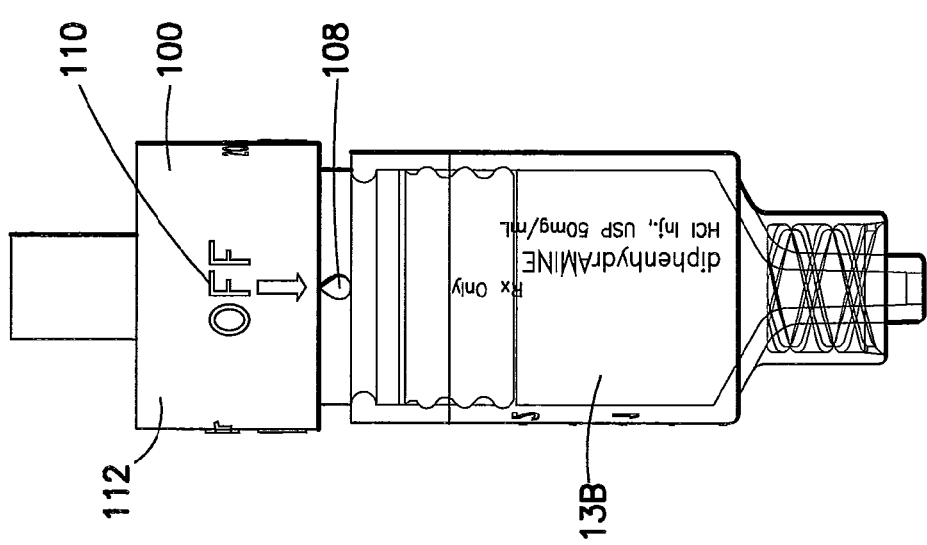
FIG. 16 is a perspective view of the pre-filled pod and regulator in an initial position having the "off" speed selected in accordance with an embodiment of the present invention.

Referring to FIGS. 16-18, the interval setting of the regulator 100 may be established by the medical practitioner. During use, the medical practitioner may set the regulator from the "off" position, shown in FIG. 16, to a metered dose position, shown in the pre-use state in FIG. 17, and in the after-use or dispensed state in FIG. 18. The medical practitioner may align an activation trigger 108 with a corresponding indicator 110 positioned on a moveable portion 112 of the regulator 100. The corresponding indicator 110 may include indicia, such as 20 ml/hr, which indicates to the medical practitioner the appropriate setting for expelling the substance 13B.

Figure 19:
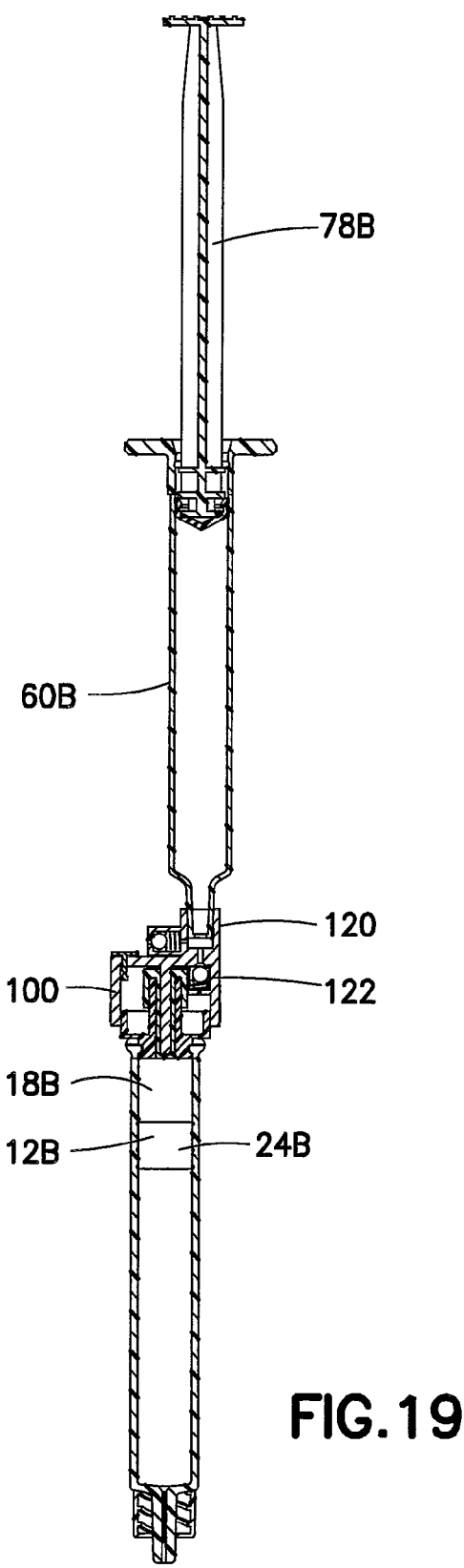
FIG. 19 is a cross-sectional front view of a pre-filled pod and regulator engaged with a standard syringe and a dispensing assembly in an initial position in accordance with an embodiment of the present invention.
Figure 20:
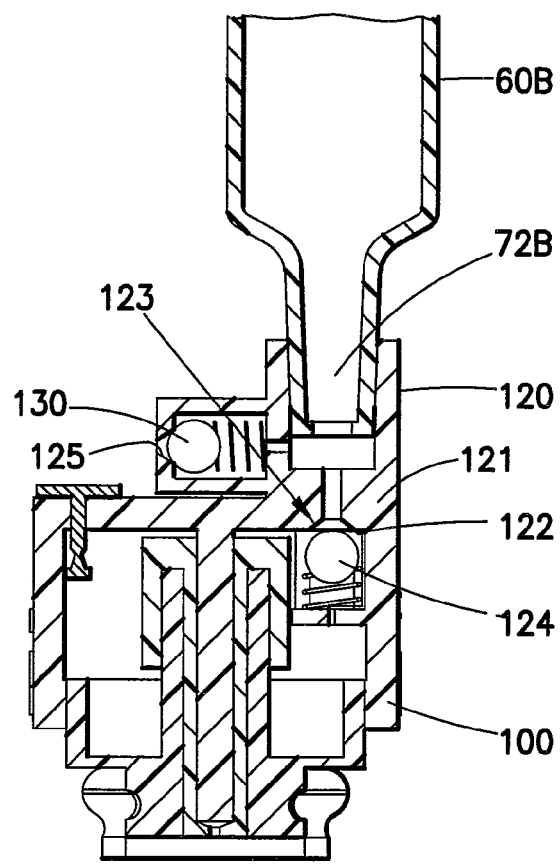
FIG. 20 is a cross-sectional front view of the regulator of FIG. 19 in accordance with an embodiment of the present invention.
Figures 21, 22:
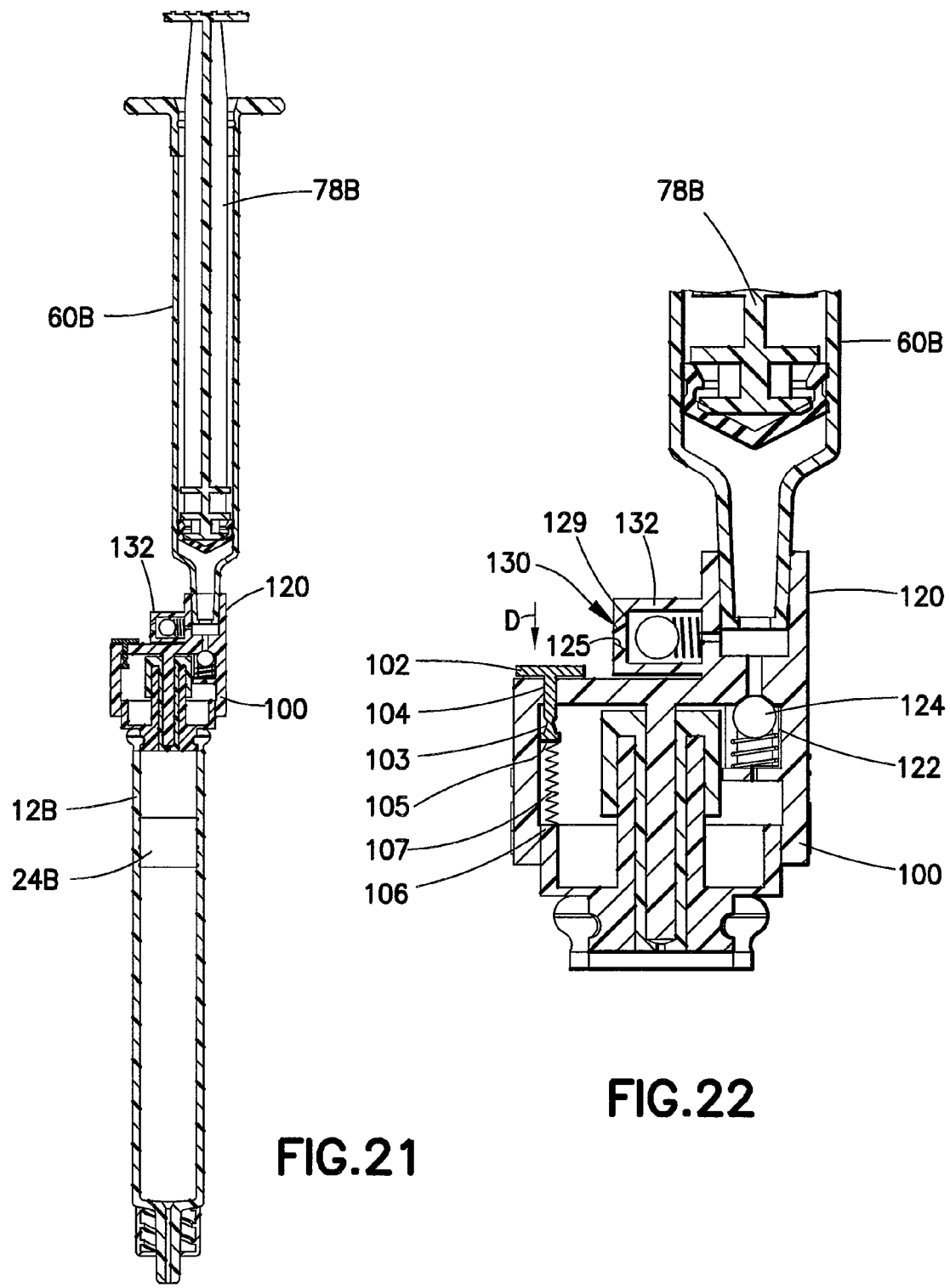
FIG. 21 is a cross-sectional front view of a pre-filled pod and regulator engaged with a standard syringe and a dispensing assembly of FIG. 19 in an activated position in accordance with an embodiment of the present invention.
FIG. 22 is a cross-sectional front view of the regulator of FIG. 21 in accordance with an embodiment of the present invention.

Referring to FIGS. 19-22, the metered dose dispensing of the regulator 100 is accomplished by providing the regulator in engagement with the pre-filled pod 12B such that the regulator 100 is in fluid communication with the proximal end 18B of the pre-filled pod 12B. A standard syringe assembly 60B is provided in fluid engagement with a first access port 120 of the regulator 100 such that the outlet opening 72B is aligned with the first access port 120. The housing 121 of the regulator 100 includes a cavity 122 aligned with the first access port 120 including a transitionable valve member 124. During operation, as shown in FIGS. 19-20, the plunger rod 78B of the syringe assembly 60B is deployed, as shown in FIGS. 12-13, which directs pressurized gas into the first access port 120. During the introduction of pressurized gas into the first access port 120, the transitionable valve member 124, such as a ball check valve, is transitioned to allow passage of air into the regulator 100. After injecting all of the gas into the first access port 120 of the regulator 100, the clinician may aspirate the syringe assembly 60B and re-deploy the plunger rod 78B, as shown in FIGS. 14-15. Referring to FIGS. 21-22, during aspiration, a second transitionable valve member 130, such as a ball check valve, is transitioned to allow ingress of air through a second access port 125 from the atmosphere.

Referring specifically to FIG. 20, during deployment of the plunger rod 78B, the transitionable valve member 124 is deployed to allow air to pass into the regulator 100 and to allow pressurization of the regulator 100. Referring to FIG. 22, when pressurized air is not being directed into the regulator 100 by deployment of the plunger rod 78B, then the transitionable valve member 124 blocks the escape of air from the regulator 100 by sealing the pathway 123, shown in FIG. 20. During aspiration, as shown in FIG. 22, the second transitionable valve member 130 is deployed to allow air to pass into the regulator 100 and interior chamber of the syringe assembly 60B through pathway 129. Referring to FIG. 20, when air is not being withdrawn from atmosphere into the regulator 100, the second transitionable valve member 130 blocks the escape of air from the regulator 100 by sealing the pathway 129, shown in FIG. 22. After the regulator 100 is properly pressurized, the indicator 102, shown in FIG. 15, is activated and the medical practitioner may disconnect the syringe assembly 60B from the regulator 100. The medical practitioner then aligns the activation trigger 108 with a corresponding indicator 110 of the regulator 100, as shown in FIGS. 16-18, and the regulator 100 introduces a proper pressure to the transitionable stopper 24B to expel the substance 13B at an appropriate dosing. The regulator 100 ensures that a proper amount of pressurized air is applied to the transitionable stopper 24B throughout the metered dosing by suitable valve means. Optionally, the indicator 102 may be adapted to relieve pressure from within the regulator 100 in the event that the regulator 100 is over pressurized. As shown in FIG. 22, an undercut 103 at the base of the indicator 102 may allow air to leak between the indicator 102 and the surrounding housing 104 once the indicator 102 is deployed in a direction shown by arrow D of FIG. 22 past a specified point. In another embodiment, a spring 107 may be disposed within the regulator 100 between a lower end 105 of the indicator 102 and a contact surface 106 of the regulator 100 to bias the indicator 102. Once the indicator 102 is deployed against the bias of the spring 107, air may pass from within the regulator 100 to the atmosphere through the undercut 103 between the indicator 102 and the surrounding housing 104. In accordance with an additional embodiment, the syringe assembly may be replaced by a finger pump, a longitudinally collapsing bellows, or a "squeeze ball" mechanism.

Figure 23:
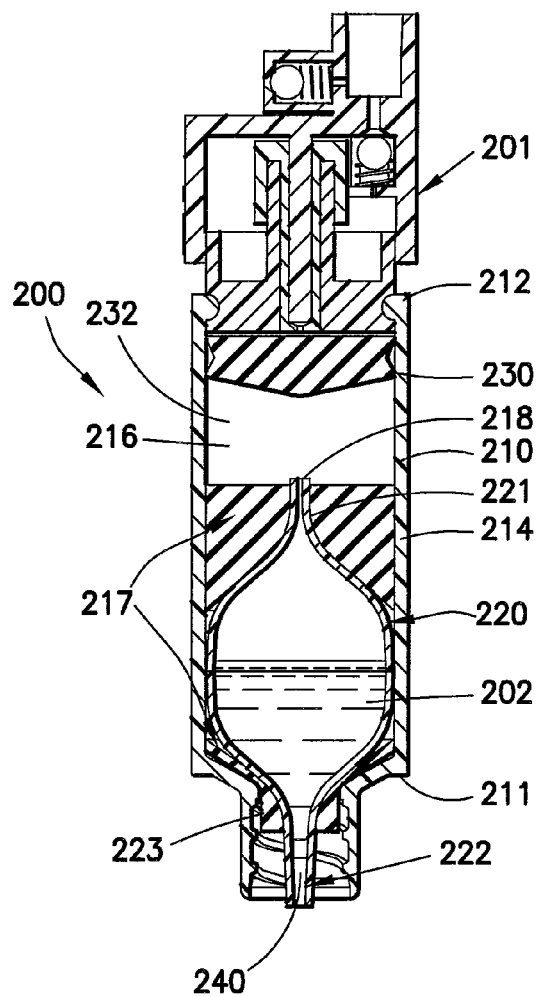
FIG. 23 is a cross-sectional front view of a pre-filled pod and regulator having an interior glass capsule in an initial position in accordance with an embodiment of the present invention.
Figure 24:
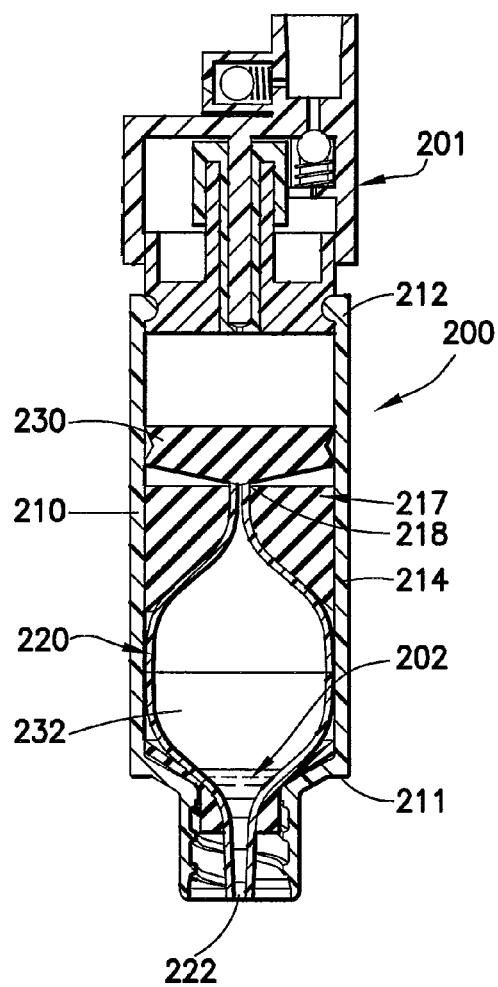
FIG. 24 is a cross-sectional front view of a pre-filled pod and regulator having an interior glass capsule in an activated position in accordance with an embodiment of the present invention.

In accordance with yet another embodiment, as shown in FIGS. 23-24, a pre-filled pod assembly 200 and regulator 201 are shown, as described herein, with the exception that the pre-filled pod assembly 200 includes a capsule 220 for containing a substance 202 disposed therein, such as fluid medication, sterile water, saline, fluid narcotic, or other controlled substance. The pre-filled pod assembly 200 may include a pre-filled pod 210 having a distal end 211, a proximal end 212, and a sidewall 214 extending therebetween defining an interior 216. The capsule 220 is disposed within the interior 216 of the pre-filled pod 210 and may be held within the interior 216 in a specific orientation by at least one grommet 217, such as a rubber grommet 217. The capsule 220 may include a first opening 218 adjacent a first end 221 of the capsule 220 and a second opening 222 adjacent a second end 223 of the capsule 220. The first opening 218 may be aligned with the proximal end 212 of the pre-filled pod 210 and the second opening 222 may be aligned with the distal end 211 of the pre-filled pod 210. In a further embodiment, the pre-filled pod 210 further includes a transitionable stopper 230, as described herein. The first opening 218 of the capsule 220 may be aligned such that in operation, as the transitionable stopper 230 is advanced or moved in a downward direction, as shown in FIG. 24, air 232 disposed over the capsule 220, as shown in FIG. 23, is pressurized and enters the capsule 220, as shown in FIG. 24, via the first opening 218. The pressurized air 232 entering the capsule 220 expels the substance 202 from within the capsule 220 through the second opening 222 and out the pre-filled pod assembly 200.

As shown in FIG. 24, at least a portion of the transitionable stopper 230 seals the first opening 218. In one embodiment, the volume of substance 202 is greater than the volume of air 232, which limits expulsion of the air 232 from the capsule 220 of the pre-filled pod 210. In order to ensure that air is not expelled from the capsule 220, in certain embodiments, the pre-filled pod 210 is oriented such that the regulator 201, or optional syringe assembly (not shown), is always higher than the pre-filled pod 210. In another configuration, the second opening 222 of the capsule 220 is dimensioned such that due to surface tension forces, the substance 202 does not exit the second opening 222 unless sufficient pressure is applied to the capsule 220 through the first opening 218. Optionally, an air bubble 240 may be provided adjacent the second opening 222 to further limit expulsion of the substance 202 absent applied pressure as discussed herein. As such, the substance 202 of the capsule 220 is isolated from the other components of the pre-filled pod assembly 200. In a further embodiment, lubrication of the capsule 220 is not required as the pressurized air provides the mechanism for expelling the substance 202 from the capsule 220. This may be advantageous as silicone oils conventionally used to lubricate the syringe assembly (not shown) or regulator 201 will not enter the capsule 220, thus limiting contamination of the substance 202.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A pre-filled pod assembly comprising:
    a pre-filled pod having a distal end, a proximal end, and a sidewall extending therebetween defining an interior;
    a transitionable stopper disposed within the interior of the pre-filled pod; and
    a regulator coupled to the proximal end of the pre-filled pod and provided in fluid communication with the interior of the pre-filled pod comprising:
    an inlet, an outlet, and a housing defining a cavity between the inlet and the outlet;
    a valve that controls flow through the inlet and into the cavity; and
    an outlet valve that controls flow out of the cavity and through the outlet;
    wherein when the valve and the outlet valve are both in a closed position, the cavity is sealed, and when the valve is in an open condition, pressurized gas or fluid may enter the cavity, and when the outlet valve is in an open position, pressurized gas or fluid stored in the cavity may pass through the outlet, and wherein the outlet of the regulator is in fluid communication with the interior of the pod such that pressurized gas or fluid flowing from the outlet of the regulator enters the interior of the pod advancing the transitionable stopper from an initial position to an activated position in which at least a portion of a fluid contained within the interior of the pre-filled pod is advanced therefrom.

2. The pre-filled pod assembly of claim 1, wherein the outlet valve supplies pressurized gas or fluid to the transitionable stopper in a predetermined amount.

3. The pre-filled pod assembly of claim 1, further comprising a standard syringe in fluid communication with the inlet of the regulator, such that depression of a plunger rod of the standard syringe opens the valve and forces pressurized gas into the cavity of the regulator.

4. The pre-filled pod assembly of claim 3, further comprising a second valve controlling flow from an air or fluid source into the inlet, wherein aspiration of the syringe opens the second valve allowing air or fluid to enter the syringe.

5. The pre-filled pod assembly of claim 4, wherein the air or fluid source is the atmosphere surrounding the regulator.

6. The pre-filled pod assembly of claim 4, wherein repeated depression and aspiration of the syringe when the outlet valve is closed causes pressure to build in the cavity.

7. The pre-filled pod assembly of claim 1, wherein the regulator further comprises an indicator that is activated when a pressure of pressurized gas or fluid stored in the cavity is sufficient to advance the desired amount of liquid from the interior of the pod.

8. The pre-filled pod assembly of claim 1, wherein the regulator comprises an activation trigger configured to be aligned with an indicator for allowing a user to open the outlet valve and set the flow through the outlet valve to advance the liquid at a metered rate.

9. The pre-filled pod assembly of claim 1, wherein introduction of pressurized gas or fluid into the inlet builds pressure in the cavity when the outlet valve is closed and closing the inlet valve causes the pressurized gas or fluid in the cavity to be stored in a pressurized state.

10. The pre-filled pod assembly of claim 1, wherein the cavity has a fixed volume.

* * * * *